United States Patent [19]
Gross

[11] Patent Number: 5,403,284
[45] Date of Patent: Apr. 4, 1995

[54] AUTOMATIC LUMEN SHUT-OFF

[75] Inventor: James R. Gross, Wareham, Mass.

[73] Assignee: The Kendall Company, Mansfield, Mass.

[21] Appl. No.: 186,953

[22] Filed: Jan. 27, 1994

[51] Int. Cl.⁶ ..................... A61M 39/04; A61M 5/00
[52] U.S. Cl. ..................... 604/167; 604/256
[58] Field of Search ............ 604/167, 256, 281, 282, 604/229, 236, 249

[56] References Cited

U.S. PATENT DOCUMENTS

| | | | |
|---|---|---|---|
| 4,560,378 | 12/1985 | Weiland | 604/256 |
| 4,612,010 | 9/1986 | Hamacher et al. | 604/229 |
| 4,740,203 | 4/1988 | Hoskins et al. | 604/236 |
| 4,863,442 | 9/1989 | DeMello et al. | 604/282 |
| 4,886,506 | 12/1989 | Lovgren et al. | 604/222 |
| 4,886,507 | 12/1989 | Patton et al. | 604/284 |
| 4,960,412 | 10/1990 | Fink | 604/256 |
| 4,976,688 | 12/1990 | Rosenblum | 604/282 |
| 5,098,394 | 3/1992 | Luther | 604/167 |
| 5,195,980 | 3/1993 | Catlin | 604/256 |
| 5,261,895 | 11/1993 | Kablik | 604/256 |
| 5,308,336 | 5/1994 | Hart et al. | 604/256 |

*Primary Examiner*—Paul J. Hirsch
*Attorney, Agent, or Firm*—Alvin Isaacs

[57] ABSTRACT

The invention features a needle and a housing having a proximal inner surface and a distal inner seat leading to and defining a lumen, wherein the needle is slidable through the housing to occupy the lumen. The housing contains and is cooperable with a valve shaped so as to sealably fit against the housing distal inner seat, the valve including a hole alignable with the lumen. When the needle slidably occupies the housing, the valve hole, and the lumen, the valve is prevented from sealably fitting against the housing distal inner seat. The housing also contains an outward biasing means biased against the valve. Upon removal of the needle from the housing, the outward biasing means urges the valve sealably against the housing distal inner seat so as to prevent flow of fluid or air through the lumen.

20 Claims, 5 Drawing Sheets

AUTOMATIC LUMEN SHUT-OFF

FIELD OF THE INVENTION

The invention relates in general to a thoracentesis device which is used in the removal of fluid from the pleural cavity, and specifically to a thoracentesis device which prevents air entry into the pleural cavity.

BACKGROUND OF THE INVENTION

It is an object of the invention to perform the medical procedure know as thoracentesis, i.e., removal of intrathoracic fluid, air or blood, or other secretions from the pleural cavity, without allowing air to be pulled from outside of the body into the pleural cavity.

SUMMARY OF THE INVENTION

The invention features a needle and a housing having a proximal inner surface and a distal inner seat leading to and defining a lumen, wherein the needle is slidable through the housing to occupy the lumen. The housing contains and is cooperable with a valve shaped so as to sealably fit against the housing distal inner seat, the valve including a hole alignable with the lumen. When the needle slidably occupies the housing, the valve hole, and the lumen, and thus the valve hole and lumen are aligned longitudinally with the longitudinal axis of the needle, the valve is misaligned longitudinally with respect to the housing distal inner seat and thus prevented from sealably fitting thereto. The housing also contains an outward biasing means biased against the valve. Upon removal of the needle from the housing, the outward biasing means urges the valve longitudinally to sealably fit against the housing distal inner seat so as to prevent flow of fluid or air through the lumen.

In preferred embodiments of the invention, the valve is cone-shaped and semi-rigid and the housing distal inner seat substantially conforms to the valve cone shape. The valve may be substantially spherical and semi-rigid and may include a notch, wherein the outward biasing means has a first end that urges against the notch, and the housing distal inner seat substantially conforms to the valve spherical shape.

The valve also may be shaped so as to permit slidable movement with respect to the housing distal inner seat. Thus, it may include two opposing ends, the end which contacts the housing distal inner seat terminating as a slanted edge which conforms to the slanted edge of the housing distal inner seat. The valve also may include a projection at the other end against which the outward biasing means first end urges.

In each valve embodiment of the invention, the location of the valve hole in the valve is such that, when the needle is slidably positioned in the hole and lumen, the valve is prevented from sealably fitting against the housing distal inner seat. For example, the hole may be off-center with respect to the center of the valve itself such that when the valve hole is aligned with the lumen, the valve itself is misaligned with the lumen and thus obstructed from sealably fitting against the housing distal inner seat.

The outward biasing means may include a coil spring, a flat spring, or a wire compressed such that the first and second ends urge outward.

The housing may further contain a washer positioned between the valve and the outward biasing means first end. The washer thus provides a flat surface against which the biasing means urges and provides uniformity of pressure on the valve. The washer also prevents forward movement of the needle in the housing, valve hole, and lumen.

The catheter tube may include a soft tip. The housing may be connected to the catheter tube via a bifurcated hub comprising two converging conduits, one conduit being in communication with the housing.

In other preferred embodiments, the housing includes a distal outer end and the device further includes a catheter tube connected to the housing distal outer end, the tube comprising a lumen which is in fluid or air communication with the housing inner seat, the lumen being sealable from the external environment when the valve is sealingly fitted against the housing inner seat. Preferably, the catheter tube includes an integral soft tip.

In yet other embodiments, the device further comprises a syringe defining a chamber and a plunger slidable within the syringe chamber. The plunger may include a compressed spring wound around the plunger and biased against the plunger and the syringe so as to urge the plunger out of the syringe chamber and thus create a negative atmospheric pressure in the syringe chamber. The syringe is attached to the housing proximal end such that the syringe chamber is in fluid or air communication with the flowpath defined by the needle, and thus may create a negative atmospheric pressure therein. The syringe may contain an anti-coagulant solution for preservation of pleural effusion collected therein for subsequent laboratory analysis.

The invention also includes methods of performing thoracentesis, comprising inserting a lumen shut-off device described herein into the body of a patient until the needle encounters the pleural cavity, the needle defining a flowpath communicating with the pleural cavity wherein needle encounter with the pleural cavity is determined by detecting a change in pressure through the plunger of the syringe.

Preferably, the method also includes the step of removing the needle from the patient after encounter with the pleural cavity, wherein upon removal of the needle the outward biasing means urges the valve sealingly against the housing inner seat to prevent air flow therethrough.

In a related aspect, the invention features a catheter for performing thoracentesis, comprising a catheter tube defining a lumen through which a needle slides, the tube having a leading end comprising an integral soft tip and a trailing end comprising an automatic lumen shut-off component, wherein upon removal of the needle from the tube, the lumen shut-off is operative to seal the lumen from air or fluid communication with an external environment.

Preferably, the lumen shut-off component is any mechanism for sealing the catheter lumen from an external environment, including those components described herein, or other components described in the art. The integral soft tip may include a side wall having inner and outer surfaces, the side wall comprising a port hole for fluid communication between the inner and outer surfaces. The integral soft tip may be any length between about 1/16 and 8/16 of an inch in length; preferably, the soft tip is ⅛ of an inch in length. The catheter tube may be made of any biocompatible material, e.g., polyurethane, the integral soft tip being made of a softer polyurethane than the catheter tube shaft. Preferably, the soft tip is made integral with the catheter tube by insert molding.

Other features and objects will become apparent from the description of the invention and from the claims.

DESCRIPTION OF THE PREFERRED EMBODIMENT

Thoracentesis involves the insertion of a tube or catheter through the chest wall or back into the pleural cavity. After insertion of the leading end of the catheter into the body, a negative pressure source, e.g., a syringe or vacuum bottle, is connected to the device in order to remove fluid from the pleural cavity through the catheter. In order for the lungs to remain expanded during the insertion procedure, there must be no positive pressure within the pleural cavity. It is important to insure that the pleural cavity remain sealed at all times from atmospheric pressure. Thus, removal of fluid from the pleural cavity presents problems unique to this body cavity. Any air or fluid leak between the pleural cavity and the atmosphere can result in a sudden rush of air from outside the body into the pleural cavity, resulting in collapse of the lung or pneumothorax.

Figure 1:
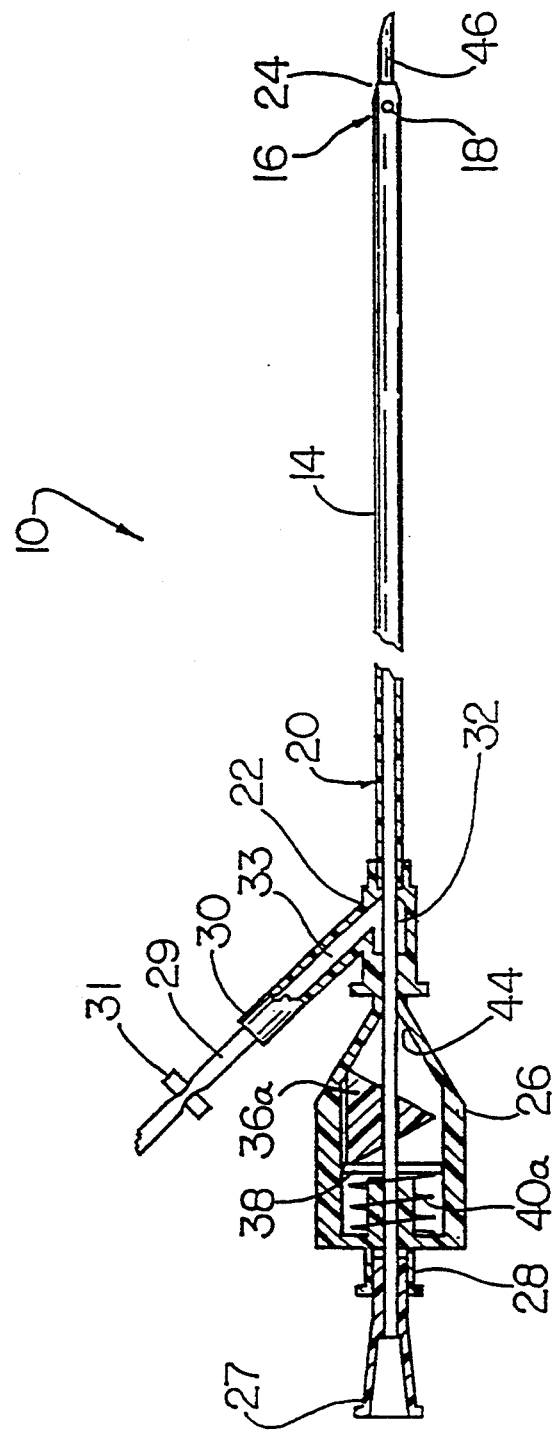
FIG. 1 is a view in partial cross-section of an automatic lumen shut-off device of the invention attached to a catheter.

A thoracentesis device of the invention 10 is shown generally in FIG. 1. The device 10 includes an elongated flexible catheter 14 having a leading end 16 formed with one or more radial ports or openings 18 which allow for fluid or air communication with the body cavity to which the leading end is inserted. The catheter leading end 16 may be tapered as shown 24. The catheter 14 has a leading end 20 connected to an bifurcated conduit 22 that is in line with the lumen 32 defined by catheter 14 and with lumen 33. The conduit 22 includes hollow barrel 26 and adapter 28 which connects snugly to barrel 26 at its proximate end. Adapter 28 and barrel 26 are aligned such that they define a space which leads to lumen 32. Conduit 22 also includes side arm 30 which feeds into the lumen 32.

For ease of description, the ends of the components of the device described herein are referred to as leading and trailing; i.e., the leading end referring to the end which encounters the body first upon insertion or which is closer to the body during use. The ends of the housing itself are referred to as proximal, i.e., the end closest to the user of the device, and distal.

In accordance with the present invention, barrel 26 includes an automatic valve which serves to shut-off air or fluid flow through catheter 14 to or from outside the body. Thus, the automatic valve includes sealing body 36a and an outward biasing means 40a, e.g., a spring, which cooperate to seal off catheter 14 from the atmosphere. The valve may also include an optional washer 38 positioned between sealing body 36a and outward biasing means 40a. Briefly, spring means 40a is biased against adapter 28 at one end and washer 38 at the other end. In all embodiments, a hollow needle 46 having a sharpened leading end is adapted to slide through a hole in the sealing body 36a and to extend through the elongated conduit 22 and catheter 14, and beyond the leading end 16 of catheter 14 if desired.

In accordance with the invention, the automatic valve is automatic, or self-sealing, and is operable to re-seal the lumen 32 of elongated conduit 22 upon withdrawal of the needle from the conduit 22. Thus, withdrawal of the needle 46 from the catheter 14 is effected by pulling the needle 46 back and out of lumen 32. Spring means 40a urges sealing body 36a into sealing position against inner seat 44 of barrel 26 when needle 46 is withdrawn. The sealing body 36a is shaped so as to fit sealingly into the inner seat 44 of barrel 26 and thus to close the lumen 32 to the outside. Several embodiments of spring means 40a and sealing body 36a are described herein. In all embodiments, the automatic valve is designed so that re-insertion of the needle after it has been fully withdrawn is prevented.

Figure 2:
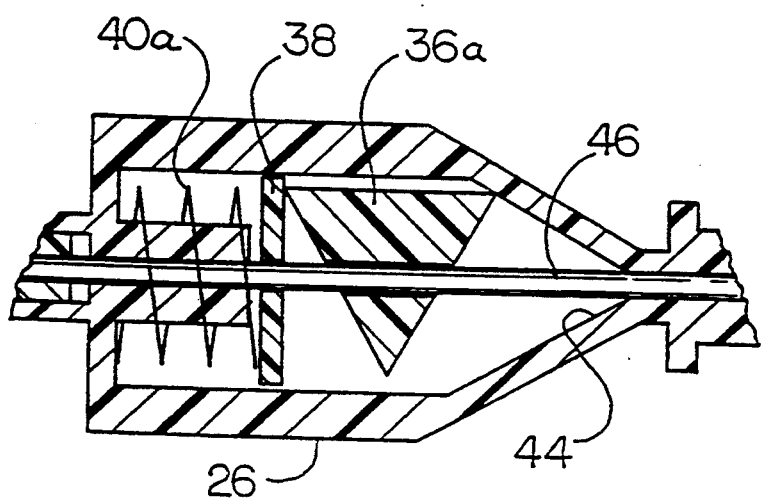
FIG. 2 is an enlarged cross-sectional view of one embodiment of the automatic lumen shut-off device of FIG. 1 in which the needle is inserted.
Figure 3:
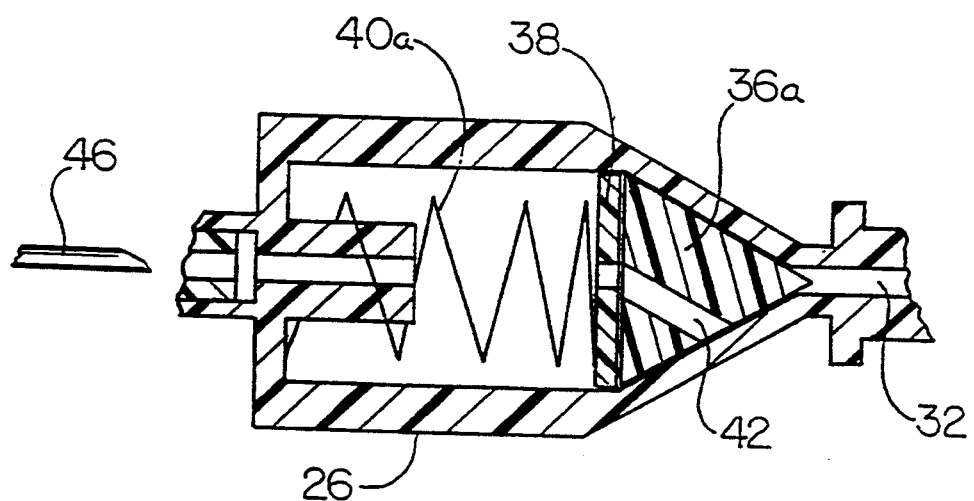
FIG. 3 is an enlarged cross-sectional view of the same embodiment of the automatic lumen shut-off device of FIG. 2 in which the needle is removed.

FIG. 2 is a schematic representation of one embodiment of a sealing body. In this embodiment, sealing body 36a is substantially triangular shaped in cross-section and is substantially cone-shaped in its three-dimensional configuration and includes passageway 42, which is sufficiently narrow to allow a needle 46 to pass therethrough without allowing air or fluid to leak around the body of the needle. In this embodiment of the invention, as in other embodiments, the inner seat 44 of the barrel 26 is shaped so as to sealingly conform to the shape of the sealing body 36a when it is in a sealing position in the barrel 26. As shown in enlargement in FIGS. 2 and 3, sealing body 36a may occupy one of two positions in barrel 26, an unsealed or sealed position. In the unsealed position depicted in FIG. 2, the needle 46 has passed through sealing body 36a and is aligned with lumen 32. In the sealed position depicted in FIG. 3, the needle 46 has been removed from passageway 42 of sealing body 36 and the sealing body has assumed a position within barrel 26 which seals off lumen 32 from the outside. Thus, in the sealed position, neither air nor fluid can pass from the outside to lumen 32 in catheter 14.

Figure 4:
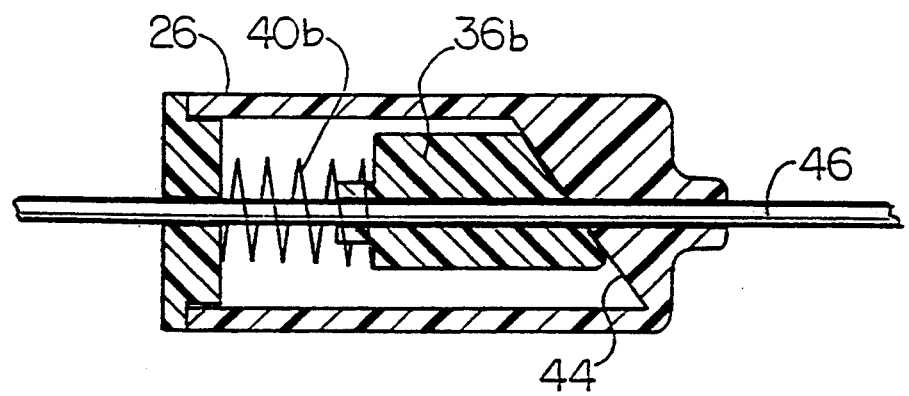
FIG. 4 is an enlarged cross-sectional view of another embodiment of the automatic lumen shut-off device of FIG. 1 in which the needle is inserted.
Figure 5:
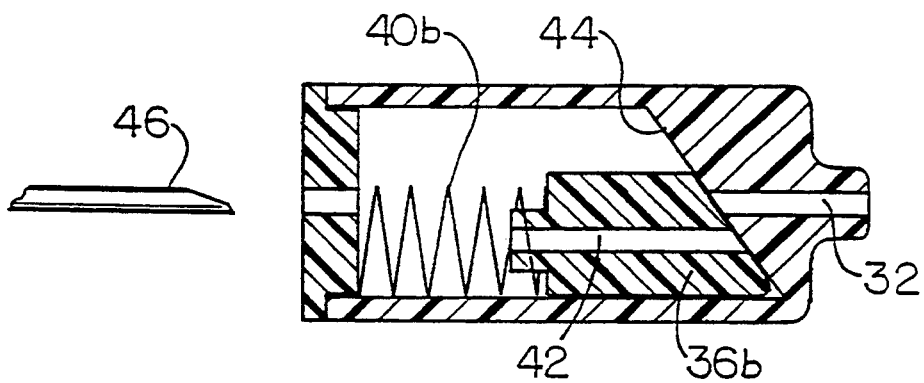
FIG. 5 is an enlarged cross-sectional view of the same embodiment of the automatic lumen shut-off device of FIG. 4, in which the needle is removed.

FIGS. 4 and 5 depict another embodiment of the sealing body, in which the valve 36b includes two opposed end sections, one end section comprising two opposed edges which form a slant at that opposed end. The slanted end contacts the housing distal inner seat 44, which is also at a slant. In FIG. 4, a needle 46 is inserted through passageway 42 of sealing body 36b, thus aligning the needle with lumen 32. FIG. 4 thus depicts the sealing body 36b in the unsealed position. In FIG. 5, the needle 46 has been removed, thus allowing spring 40b to urge sealing body 36 to slide sideways within barrel 26; passageway 42 in sealing body 36b and lumen 32 are thus misaligned. FIG. 5 thus depicts the sealing body 36b in the sealed position such that no air or fluid can enter from the outside into catheter 14.

Figure 6:
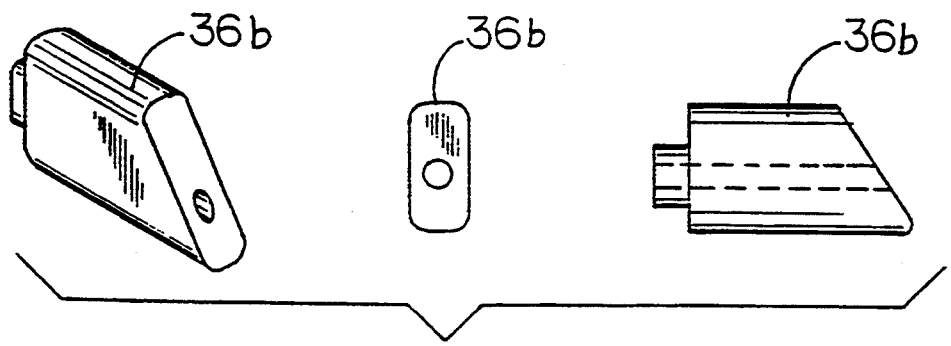
FIG. 6 shows perspective, front, and side views, from left to right, respectively, of the valve portion of the device of FIGS. 4 and 5.

FIG. 6 shows different views of the sealing body 36b of FIGS. 4 and 5. The left-most view in FIG. 6 is a perspective view of the sealing body 36b; the middle view is a front end view showing passageway 42 in the center; and the right-most view is a side view essentially as shown in FIGS. 4 and 5.

Figure 7:
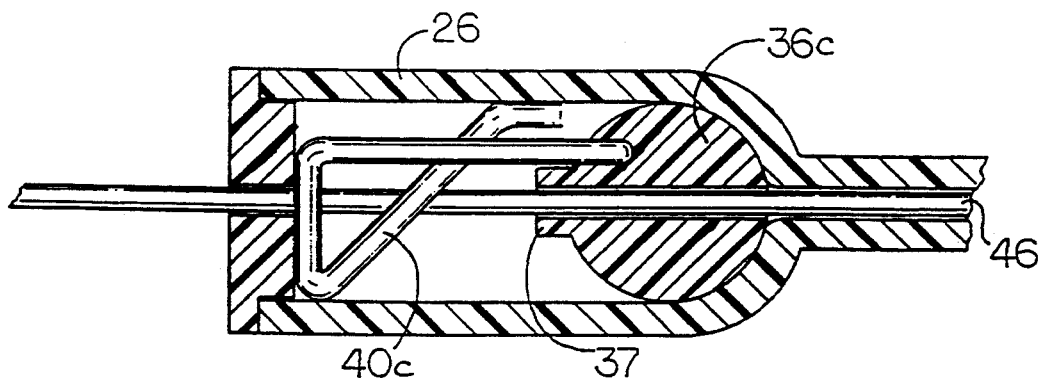
FIG. 7 is an enlarged cross-sectional view of yet another embodiment of the automatic lumen shut-off device of FIG. 1 in which the needle is inserted.
Figure 8:
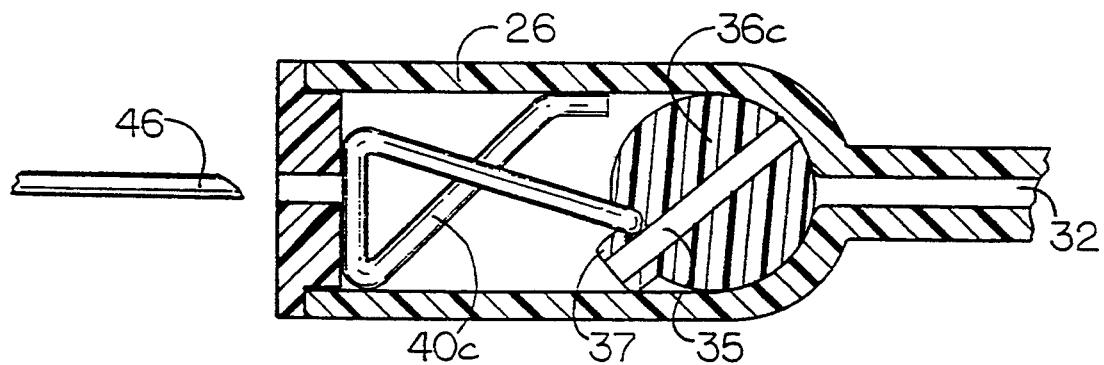
FIG. 8 is an enlarged cross-sectional view of the same embodiment of the automatic lumen shut-off device of FIG. 7, in which the needle is removed.

Referring to FIGS. 7–8, yet another embodiment of the sealing body is a semi-rigid substantially spherical body 36c having a hole 35 therethrough for passage of needle 46. The spherical sealing body will include a notch 37 extending from the sphere. The outward biasing means may be a flat spring 40c or a wire which is biased against the housing 26 at one end and against the notch 37 at the other end. Insertion of the needle through the spherical body 36c and the lumen 32 prevents the sphere from rotating and thus keeps the lumen 32 open for movement of the needle therethrough. Removal of the needle 46 from the housing 26, the biasing means 40c pushes on notch 37, thus causing hole 35 and lumen 32 to misalign and sealing the lumen 32 from fluid or air leaks.

In all embodiments of the automatic valve of the invention, the seal between sealing body and the inner seat 44 of barrel 26 is created by an extremely snug fit between the closely conforming shapes of the sealing body and the inner seat 44 of barrel 26.

Figure 9:
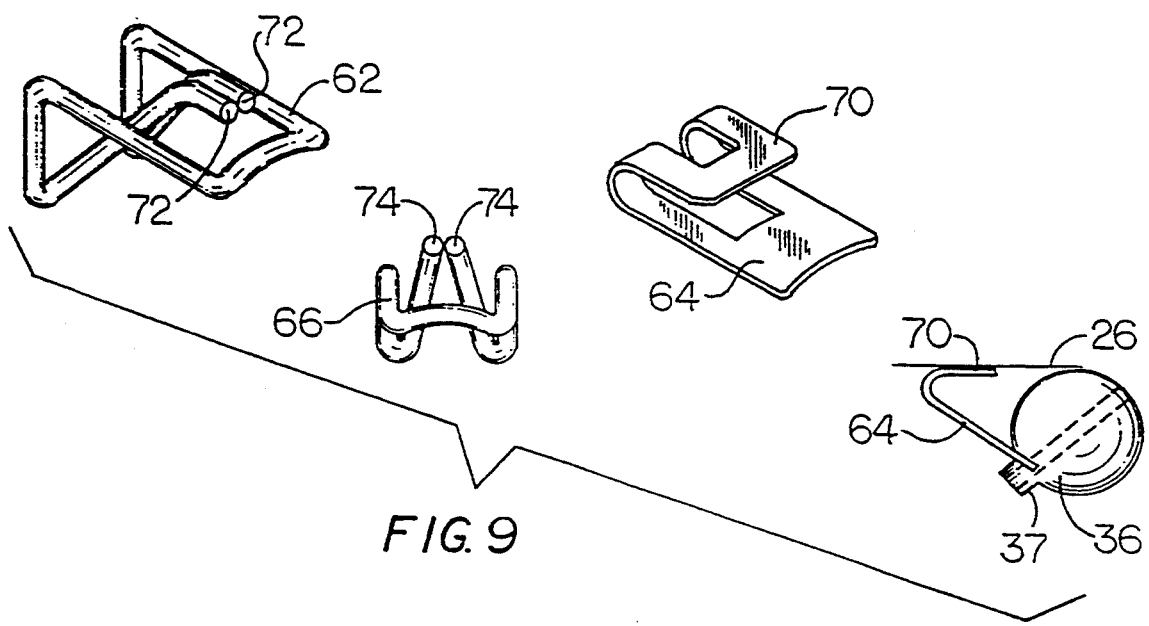
FIG. 9 shows alternate embodiments of the spring portion of the device shown enlarged in FIGS. 2–8, along with one alternate spring in cooperation with the valve embodiment shown in FIGS. 7 and 8.

The outward biasing means of the inventive device may be of any shape which allows it to urge the sealing body into the inner seat of the barrel. The outward biasing means may include a coiled spring, as shown in FIGS. 1–5, or a simple wire which is contorted into a shape which creates a tension in the wire, as shown in FIGS. 7 and 8. Alternatively, as shown in FIG. 9, the biasing means may be a flat spring 62, 64, or 66, which includes a protrusion 70 or arms 72 or 74 which create an outward bias. For example, flat spring 64 may cooperate with valve 36 by urging against the housing 26 at the protrusion 70 end and notch 37 at the other end.

Needle 46 is sized so as to pass freely through the lumen 32 of conduit 22 and all the way through the catheter 14 so that the beveled leading end of needle 46 extends a short distance beyond the leading end 16 of catheter 14. At its trailing end, the needle 46 is attached to a connector 27 which is engageable with adapter 28 to limit axial movement of the needle 46 relative to adapter 28.

The sealing body is made of a semi-rigid material such that the beveled end of needle 46 can pass therethrough. This sealing body material may be, for example, a semi-rigid plastic.

Side-arm 30, which defines lumen 33 that also leads into lumen 32, is for removal or delivery of liquid through the catheter 14. Side-arm 30, leading to extension tube 29, will normally be maintained such that it is blocked, e.g., using a clamp 31 or similar means around extension tube 29. Side arm 30 may be connected via a tube to a vacuum bottle or the like. Thus, in withdrawal of fluid, e.g., the vacuum bottle is used to collect fluid or other matter from the pleural cavity. In addition, the rate of fluid removal from the body may be controlled using the clamp, e.g., a roller clamp.

Catheter 14 will preferably include a soft or blunted tip. For example, the catheter tip may be insert-molded or injection-molded into a shape which blunts the tip enough to avoid piercing the lung, but not enough to prevent entry of the tip into the body cavity. For example, the shape of the tip may be altered to provide a blunt effect, e.g., by narrowing the tip in a cone shape, and then flaring the edge back. Alternatively, the narrowed, cone-shaped tip may be over-molded with an integral tip of a softer material than the remainder of the catheter shaft. The integral soft tip may include, in addition to the lumen opening at its leading end, a side wall having inner and outer surfaces and a port hole through the side wall for fluid communication between the inner and outer surfaces. The integral soft tip may be any length between about 1/16 and 8/16 of an inch in length, and may be made by insert molding as follows.

A mold is provided which is capable of forming the catheter tip into the desired shape. The softer portion of the catheter tip may measure, e.g., about ⅛ of an inch. The leading end of the catheter tube0, including an open end, is placed into the mold, and a pin is inserted into the open end of the catheter tip to preserve the lumen of the catheter during molding. A molten plastic of lower durometer is injected into the mold around the catheter leading end, and the plastic is allowed to cool and harden. The newly-formed soft tip is then removed from the mold. Materials of lower durometer may be used to form the soft integral catheter tip which is softer than the material from which the catheter tube itself is made. The catheter tube may be made of an elastomeric material such as polyurethane, and the tip made of a lower durometer polyurethane. For example, the catheter tube may be made of Tecoflex (Woburn, Mass.) medical grade aliphatic polyurethane 100A, and the tip of polyurethane 60A or 80A. The softer-tipped catheter tip will be less likely to damage the lung during insertion of the catheter into the body.

Figure 10:
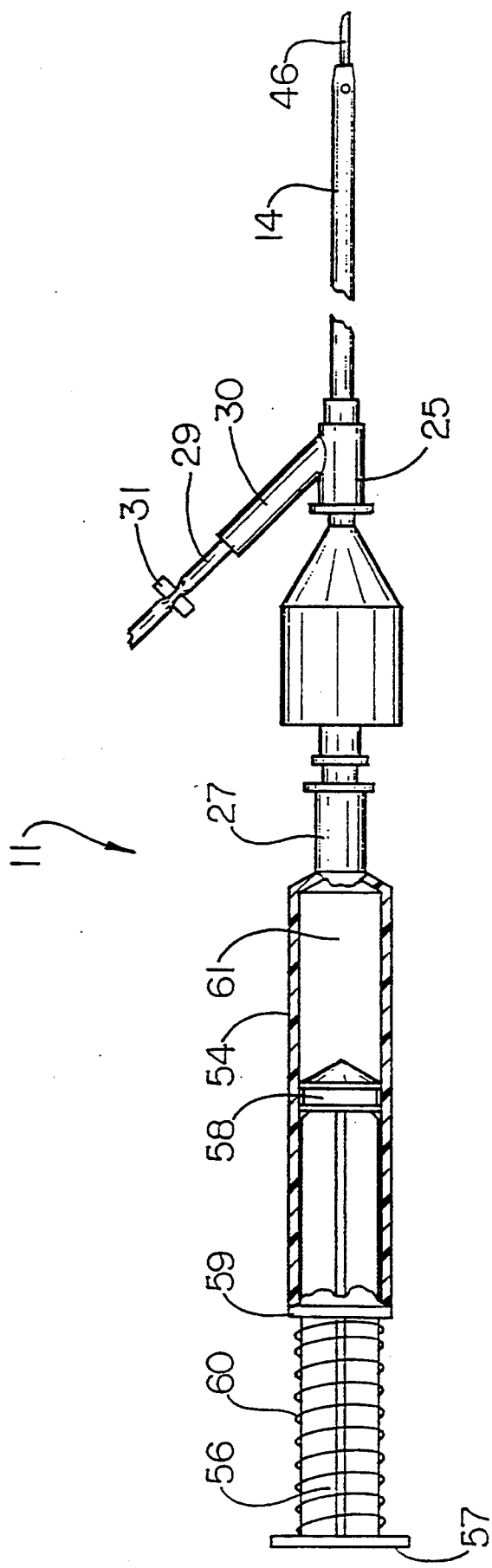
FIG. 10 is a catheter connected with a plunger and syringe in which the plunger/syringe portion is shown in partial cut-away.

In a preferred embodiment of the invention shown in FIG. 10, the device 10 includes means for applying negative atmospheric pressure within the flowpath defined by the needle, the means including a syringe/plunger combination. Thus, hub 25, which contains the automatic lumen shut-off device of the invention, is adapted via connector 27 to a syringe 54. A plunger 56 is slidable within the syringe 54 and includes gasket 58. Connector 27 contains a hole to allow the flowpath defined by needle 46 to be in air or fluid communication with the syringe chamber 61. The plunger is in pressure-communication with the flowpath defined by needle 46 such that when the plunger 56 is withdrawn outwardly from the syringe 54, negative atmospheric pressure is effected in the flowpath defined by the needle 46. As shown in FIG. 10, outward movement of plunger 56 within syringe 54 may be effected by a compression spring 60 wound around the plunger and creating a bias against the plunger trailing end 57 and the syringe trailing end 59. The compression spring 60 is thus maintained under compression to create an automatic suction for location of the pleural space.

Referring to FIGS. 1–10, the devices 10 and 11 of the invention may be used in thoracentesis as follows. The beveled needled 46 is used to penetrate a chest wall of the patient and to locate the pleural cavity. The tapered end 24 of catheter 14 follows closely behind the beveled needle end 46 through the chest wall. As soon as the leading catheter end 16 is within the chest wall, negative pressure is applied within the flowpath defined by needle 46 by pulling rearwardly on plunger 56 or by allowing compression spring 60 to be released slightly such that the plunger 56 moves out of the syringe 54. Penetration of the patient's body by the needle 46 and catheter 14 is resumed. When the needle 46 passes through the chest wall and into the pleural cavity, negative pressure within the flowpath defined by the needle causes fluid in the pleural cavity to be drawn through the needle and into the syringe chamber. Thus, the syringe chamber may contain a preservative, e.g., an anti-coagulant, miscible with the pleural effusion, for preservation of the body fluids for subsequent analysis. This will be visible immediately to the surgeon such that he or she knows the needle point has reached the pleural cavity. The device is inserted slightly further to insure that the catheter leading end 16 is in the pleural cavity, but not far enough for the needle to penetrate the lung.

The needle is then removed from the catheter 14 by drawing back on the syringe 54, leaving the catheter 14 in place in the pleural cavity. The automatic lumen shut-off may include an additional safety measure with respect to forward movement of the needle. If the needle is pulled back on during the procedure, it is important for the physician to continue removing the needle. No attempt should be made to push the needle forward after partial removal in order to re-position the catheter in the body, as this seemingly minor backward and forward movement of the needle in the catheter tube shaft thus risks piercing the side wall of the catheter tube and thus entry of the needle into the body without the guidance of the tube shaft. This additional safety measure is effected by a loose fit of the washer 38 around the needle 46 such that, during withdrawal and subsequent re-insertion of the needle, the washer 38 becomes positioned at a slight angle with respect to the needle and thus acts as a frictional stop or brake with respect to forward movement of the needle. Therefore, during needle withdrawal, the needle cannot be pushed forward again through the lumen due to the presence of the washer 38 in the housing. In removing the needle 46, the syringe 54 and plunger 56 are also removed. The catheter 14 is left in place in the patient.

Upon complete removal of needle 46, the automatic lumen shut-off device of the invention forms a seal within the housing as the outward biasing means urges the valve into sealing position against the inner seat of the housing, at the portion where the housing leads to the catheter lumen 32. The seal thus created prevents air or fluid from entering or leaving through the catheter lumen 32. Thus, fluid or air communication between the pleural cavity of the patient and the outside atmosphere is completely avoided according to the invention. Once the needle is withdrawn, danger of lung puncture is substantially eliminated even if the leading catheter end 16 engages the lung since the catheter 14 is flexible and its leading tip 24 relatively soft or blunt, as described herein. Because the catheter 14 is relatively flexible in comparison to the needle 46, the danger of puncturing the lung is substantially eliminated after removal of the needle, particularly using a soft-tipped catheter 14. The catheter itself is sufficiently flexible so as to pose little threat of puncturing the lung.

Once the needle has been removed and the automatic lumen shutoff is effected, the side arm 30 may be connected to a vacuum source such as a vacuum bottle. The vacuum bottle may be used to withdraw fluid from the pleural cavity. The rate at which fluid is withdrawn from the pleural cavity is controlled by clamp 31. The tightness of the clamp on the extension tubing 29 is controlled manually.

It will be appreciated that the thoracentesis procedure described above is carried out without air or fluid communication between the pleural cavity in the patient's body and the external environment. Thus, no air is allowed to enter the pleural cavity and the threat of lung collapse is avoided. Once the leading end 16 of the catheter 14 is positioned within the pleural cavity, the lumen 32 is sealed from the atmosphere both when the needle 46 is inserted within the catheter 14 by virtue of the syringe and automatically upon removal of the needle 46 from the catheter 14 and housing 26.

OTHER EMBODIMENTS

Although the invention has been described with reference to the preferred embodiment illustrated in the drawings, other modifications of the invention will be apparent to those skilled in the art without departing from the spirit or scope of the invention.

I claim:

1. A lumen shut-off device, comprising
   a needle;
   a housing having a proximal inner surface and a distal inner seat leading to and defining a lumen, wherein said needle is slidable through said housing to occupy the lumen, said housing containing and being cooperable with:
   a valve shaped so as to sealably fit against said housing distal inner seat, said valve including a hole alignable with said lumen, wherein when said needle slidably occupies said housing, said valve hole, and said lumen, said valve is prevented from sealably fitting against said housing distal inner seat; and
   an outward biasing means biased against said valve and, upon removal of said needle from said housing, urging said valve sealably against said housing distal inner seat so as to prevent flow of fluid or air through said lumen.

2. The lumen shut-off device of claim 1 wherein said valve hole is off-center with respect to the center of the valve itself such that when said valve hole is aligned with said lumen, said valve is misaligned with said lumen and thus obstructed from sealably fitting against said housing distal inner seat.

3. The lumen shut-off device of claim 2 wherein said valve is cone-shaped and semi-rigid and said housing distal inner seat substantially conforms to said valve cone shape.

4. The lumen shut-off device of claim 1 wherein said valve is substantially spherical and semi-rigid and includes a notch, wherein said outward biasing means has a first end which urges against said notch, and said housing distal inner seat substantially conforms to said valve spherical shape.

5. The lumen shut-off device of claim 1 wherein said valve comprises two opposed end sections, said outward biasing means urging against one said end section, the other said end section including two opposed edges which form a slant at said end, and said housing distal inner seat substantially conforms to said slant.

6. The lumen shut-off device of claim 1 wherein said outward biasing means comprises a coil spring.

7. The lumen shut-off device of claim 1 wherein said outward biasing means comprises a flat spring.

8. The lumen shut-off device of claim 1 wherein said outward biasing means comprises a wire compressed such that the first and second ends of the wire urge outward.

9. The lumen shut-off device of claim 1, said housing further containing a washer positioned between said valve and a first end of said outward biasing means.

10. The lumen shut-off device of claim 1 wherein said housing is connected to a catheter tube via a bifurcated hub comprising two converging conduits, one said conduit being in communication with said housing.

11. The lumen shut-off device of claim 1, wherein said housing comprises a distal outer end, said device further comprising a catheter tube defining a lumen that is contiguous with said lumen leading from housing distal outer end, said catheter tube lumen being sealable from the external environment when said valve is sealingly fitted against said housing inner seat.

12. The lumen shut-off device of claim 11, said catheter tube comprising a soft integral tip.

13. The lumen shut-off device of claim 1, wherein said housing comprises a proximal end and said needle encompasses a flowpath, said device further comprising
   a syringe having leading and trailing ends and containing a chamber,
   a plunger having leading and trailing ends, said plunger leading end being slidable within said syringe chamber,
   a compressed spring wound around said plunger and biased against said plunger trailing end and said syringe trailing end, wherein said syringe is connected to said housing proximal outer end and said syringe chamber is in fluid or air communication with said needle flowpath.

14. The lumen shut-off device of claim 13 wherein the syringe contains an anti-coagulant.

15. A catheter for performing thoracentesis, comprising
   a catheter tube defining a lumen through which a needle slides, said tube having a leading end comprising an integral soft tip and a trailing end comprising a shaft and an irreversible lumen shut-off component, wherein upon removal of said needle from said tube, said lumen shut-off is operative to seal said lumen from fluid communication with an external environment such that said needle cannot be reinserted into said lumen.

16. The catheter of claim 15, said integral soft tip including a side wall having inner and outer surfaces, said side wall comprising a port hole for fluid communication between said inner and outer surfaces.

17. The catheter of claim 15, said integral soft tip comprising between 1/16 and 8/16 of an inch in length.

18. The catheter of claim 15 wherein said catheter tube is made of polyurethane, said integral soft tip being made of a softer polyurethane than said catheter tube shaft.

19. The catheter of claim 15 wherein said soft tip is made integral with said catheter tube by insert molding.

20. The catheter of claim 15, further comprising a needle slidably positioned in said lumen.

* * * * *